United States Patent
Livaditis

(10) Patent No.: US 6,319,007 B1
(45) Date of Patent: Nov. 20, 2001

(54) VITAL PULP THERAPY

(76) Inventor: Gus J. Livaditis, 2328 Marlboro Dr., York, PA (US) 17403

(*) Notice: Subject to any disclaimer, the term of this patent is extended or adjusted under 35 U.S.C. 154(b) by 0 days.

(21) Appl. No.: 09/624,116

(22) Filed: Jul. 24, 2000

(51) Int. Cl.[7] ............................................. A61C 5/02
(52) U.S. Cl. ..................................................... 433/224
(58) Field of Search ................................. 433/224, 215, 433/32

(56) References Cited

U.S. PATENT DOCUMENTS

| | | | |
|---|---|---|---|
| 4,674,499 | 6/1987 | Pao | 128/303.14 |
| 4,766,896 | 8/1988 | Pao | 128/305 |
| 4,805,616 | 2/1989 | Pao | 128/303.17 |
| 4,813,876 * | 3/1989 | Wang | 433/224 |
| 4,885,004 | 12/1989 | Pao | 604/22 |
| 5,421,727 * | 6/1995 | Stevens et al. | 433/224 |

OTHER PUBLICATIONS

Liebenberg, W.H., *J. Adhes. Dent.*, 1(4), 345–363 (1999).
Mitchell and Lumb, *Brit. J. of Surgery*, 50, 314–320 (1962).
Azzi et al., *J. Periodontol.*, 54(2), 96–100 (1983).
Krejci et al., *Oral Surg.*, 54(5), 575–582 (1982).
Spangberg et al., *Oral Surg.*, 54(6), 678–685 (1982).
Robertson et al., *Oral Surg.*, 46(5), 702–710 (1978).
Laws, A.J., *N.Z. Dental Journal*, 53, 68–70 (1957).
Hurd, L.M., *Archives of Otolaryngology*, 13, 442 (1931).
Greenwood, Jr., J., *Am. J. Surg.*, 50(2), 267–70 (1940).
Pao, D.S., *Arch. Ophthalmol.*, 97, 1351–1352 (1979).
Parel et al., *Arch. Ophthalmol*, 99, 494–497 (1981).
Elmed Company Brochure, (1998).

* cited by examiner

*Primary Examiner*—John J. Wilson
*Assistant Examiner*—Melba Bumgarner
(74) *Attorney, Agent, or Firm*—Synnestvedt & Lechner LLP

(57) ABSTRACT

Methods and apparatus are provided for hemostasis of dental pulps. The methods include treating a dental pulp using bipolar electrocoagulation to control the bleeding of the dental pulp.

14 Claims, 3 Drawing Sheets

VITAL PULP THERAPY

FIELD OF THE INVENTION

The present invention is directed to methods and apparatus for providing hemostasis of dental pulp. In particular, the present invention is directed to electrosurgical methods and apparatus which provide durable hemostasis to exposed dental pulp with little or no damage to the pulp.

A. The Anatomy of the Tooth

Teeth, both primary and permanent, consist of outer enamel, an inner layer of dentin, and a soft tissue component referred to as the dental pulp. The pulp is enclosed by dentin, is continuous with soft tissue in the tooth socket, begins at the tip of the root, traverses through each root and terminates in the pulp chamber of the coronal or visible portion of the tooth. Initially, the dental pulp is responsible for the development of the enamel and dentin and later continues to provide the blood supply, nerve innervation and lymphatic drainage. The pulp responds to insult by depositing reparative and secondary dentin to protect the pulp and initiates an inflammatory process to combat bacterial infection.

B. Injury to the Pulp

The tooth and pulp are typically threatened in a variety of ways: (1) fracture of the tooth exposing the pulp to bacteria normally present in the oral cavity; (2) dental caries (decay) which decalcifies enamel and dentin, exposes the pulp and allows ingress of bacteria and bacterial products, (3) dental restorative procedures which may inadvertently expose the pulp; and (4) failure of dental restorations through fracture or leakage, including microleakage, allowing bacteria or bacterial by-products to reach the pulp. For decades many factors have been blamed for causing inflammation and necrosis (i.e. non-vitality, death) of the dental pulp, including: (1) dental caries and associated bacteria being the most prominent; (2) fracture and exposure to bacteria; (3) excess heat from dental instrumentation; and (4) toxicity of dental materials. More recently, bacterial invasion via microleakage has been attributed as an important cause of pulpal inflammation and necrosis.

Traditionally, when a small exposure of the pulp occurred mechanically, by fracture of the tooth, or while excavating caries, the exposure was promptly 'capped' with various dental materials in an attempt to prevent inflammation or necrosis of the pulp. If the exposure was small and capping occurred immediately and with a suitable material, pulpal necrosis could be averted. However, if the exposure was moderate or large in size, or if capping occurred after bacteria developed a foothold, or if the capping material deteriorated leading to microleakage, then inflammation or necrosis would typically occur. Materials (e.g. calcium hydroxide) which stimulated reparative dentin formation were used for capping of the pulp for over half a century in an attempt to stimulate health and to restore the pulpal wall naturally via slow deposition of reparative dentin.

C. Treatment Methods for Exposed Pulp

If the pulp progressed to necrosis, only two options were available to the patient: (1) extraction of the tooth; or (2) extirpation of the necrotic pulp and filling of the pulpal space with a suitable material to prevent microleakage via the pulp space to the surrounding bone. This second alternative is referred to as endodontic therapy (root canal treatment). Inflamed vital dental pulps, however, represent a substantial portion of infected pulps. Additionally, pulps exposed intentionally for therapeutic purposes (e.g. to support a denture) also constitute a significant portion. These latter two groups are currently relegated to extraction or endodontic therapy despite their vitality. Inflamed but vital pulps are considered, under current clinical guidelines, to be untreatable. Even teeth with relatively mild symptoms are diagnosed as 'irreversible pulpitis' and condemned to extraction or endodontic therapy.

Over the past seven decades, the research primarily centered around the stimulation of reparative dentin deposition and pulp therapy was limited to small exposures on asymptomatic teeth. A few reported exceptions involved more aggressive pulp therapy but was limited to adolescent and young adult patients. Several developments in the field opened the possibility of more comprehensive pulp therapy. These included: (1) The realization that most pulpal inflammation is due to bacteria invasion and bacterial by-products occurring via microleakage and less due to toxicity of dental materials; and (2) The development of materials that adhere to dentin and which can produce a seal to prevent microleakage (i.e. dentin adhesion products and the ability to create a hybrid layer consisting of collagen and resin). The ability to stimulate the deposition of reparative dentin became a standard for demonstrating re-organization and healing of the pulp after an insult. Despite these developments, only teeth with small exposures or mild clinical symptoms were routinely treated while the great majority of teeth exhibiting pulpal inflammation or periapical inflammation (inflammation of a pulpal origin in the bone around the tip of the root) were treated with endodontic therapy or extraction of the tooth.

One of the obstacles in treating the pulp is the impact of bleeding on the formation of the pulp barrier (sealing of the pulp or the restoration of the missing pulpal wall). Bleeding during any surgical procedure can impact on the success of treatment ranging from (1) being a mere nuisance or compromising visibility to (2) creating a toxic reaction (as in neurosurgery). Bleeding around the retina during eye surgery, for example, is an important concern. In pulp therapy, bleeding compromises visibility, jeopardizes the dentin adhesion, and creates voids or tracts within the barrier material resulting in chronic irritation and failure of the pulp therapy. In a very common situation, pulp therapy cannot be instituted because the hemorrhaging cannot be controlled. In these cases, the teeth are relegated to endodontic therapy or extraction simply due to the uncontrolled bleeding. One might wonder why bleeding cannot be controlled in an exposure approximately 2–4 square mm in area and consisting of very small blood vessels when bleeding is routinely controlled in major surgical procedures where much larger vessels are involved. A good analogy can be made with ophthalmic surgery where even minor amounts of bleeding during the procedure can compromise the overall therapeutic effort. In pulp therapy, minor bleeding contaminates the surface of the dentin preventing adhesion of the pulp barrier and jeopardizing the valuable dentinal seal. Residual blood clots have been reported to prevent healing and even stimulate an inflammatory response by the release of chemotaxic components.

Another important dilemma is that the bleeding must be controlled with little or no injury to the remaining pulp tissue. Furthermore, hemostatic procedures and materials which do not impact on the highly technique-sensitive dentinal adhesion process must be selected. These two factors place severe restrictions on the ability to control bleeding. Furthermore, temporary hemostasis is not sufficient since numerous procedures are required to create the pulp barrier and final restoration—any of which can cause recurring bleeding at a critical moment. Therefore, durable hemostasis is required with minimal or no injury (especially lasting injury) to the pulp. The present invention provides methods and apparatus which satisfy the need in the art for durable hemostasis.

Reported Developments

Most efforts in controlling bleeding of the pulp involved application of a cotton pellet and light pressure until hemorrhaging ceased. This proved fairly effective with very small exposures but was ineffective with larger exposures or hyperemic pulps. Over the past century, pulpotomy procedures were quite common upon exposure of the pulp. Pulpotomy procedures typically remove the chamber portion of the pulp (the part of the pulp enclosed by the clinical crown, the visible portion of the tooth, as opposed to the pulp tissue contained within the root portion). This allowed control of bleeding at the more constricted portion of the pulp which was easier to accomplish. However, it meant sacrificing a substantial segment of vital pulp tissue. This approach is still quite common in children's primary teeth.

Numerous vasoconstricting (blood vessel contracting) medicaments and even necrotizing materials have been used partly for hemorrhage control and partly for therapeutic purposes. More recently, with greater attention to gentle treatment of the pulp, the selection of materials or medicaments were directed at hemorrhage control with minimal effect on the pulp tissue and with minimal impact on the dentin adhesion procedures. Sodium hypochlorite (2–5%) has been advocated for use in this manner. The present state of the art in pulpal hemostasis consists of: (1) cotton pellet—dry, moist with water, or moist with saline; (2) Sodium hypochlorite (2–5%) applied and rinsed; or (3) failing to achieve hemostasis—referral for endodontics or extraction.

Monopolar electrosurgery uses an active electrode which is very small in dimension compared to the grounding electrode (referred to as the dispersive electrode). The applied power concentrates the current at the narrow point or blade of the active electrode. When sufficiently high, the current is released to the less conductive tissue via direct contact or as a spark that jumps to the tissue. The intense heat that is generated by this sequence of events, which occurs thousands of times per second, coagulates the tissue next to the active electrode. With the monopolar mode, the current then dissipates through the body of the patient via a path of least resistance to the dispersive electrode. Serious consequences have been reported associated to this dispersive path. In particular, there is the potential for necrosis of the pulp, never before realized in dentistry and identified by the inventor, due to a channeling effect of the dissipating current passing through a constriction of the tissue. Monopolar electrosurgery has been used in pulp therapy to fulgurate the pulp. Fulguration is the destruction or ablation of tissue caused by delivering a high frequency electrosurgical current. An electrode is applied a short distance from the tissue and a series of high intensity sparks are caused to jump from the electrode to the tissue causing ablation of the tissue. Fulguration was used much like formocresol, silver nitrate, and other materials to coagulate, necrotize, cauterize, etc a layer of tissue or the entire pulp. Fulguration also provided hemostasis although it is not clear whether it was ever used solely for hemostasis. Fulguration was shown to adversely affect the pulp and tissue surrounding the tooth. The hazards of using monopolar electrosurgery on the dental pulp or near metallic restorations in the tooth, has been reported in a number of publications. These hazards are related to the monopolar mode of electrosurgery, and accordingly, monopolar electrosurgery is contraindicated for use on or near the dental pulp.

SUMMARY OF THE INVENTION

The present invention relates to a method for controlling bleeding in the exposed dental pulp in a patient comprising bipolar electrocoagulation of the pulp. The present invention includes a method for creating a coagulated tissue layer on the surface of an exposed dental pulp in order to reconstruct the pulpal wall comprising bipolar electrocoagulation of the pulp. The methods of the present invention preferably utilize a two-point bipolar electrode, or a coaxial bipolar electrode. Preferred bipolar electrodes include a fixed parallel dual-prong electrode (FPDP). Another aspect of the present invention is the provision of an apparatus for bipolar electrocoagulation of dental pulp comprising a bipolar electrode connected to a low power electrosurgical unit. Preferably this apparatus further comprises an electronic timer attached to the electrosurgical unit which regulates the duration of the power supplied to the electrode. Preferably the bipolar electrode is a coaxial electrode which limits coagulation to the surface area of the tip of said electrode. In preferred embodiments of the invention, the timer enables minimal and prescribed coagulation of tissue by the application of microsecond impulses of power to the tissue. Another aspect of the present invention provides for application of resin to the pulp. In preferred embodiments, the resin is color-coded.

DETAILED DESCRIPTION OF THE INVENTION

A. Introduction

Figure 1:
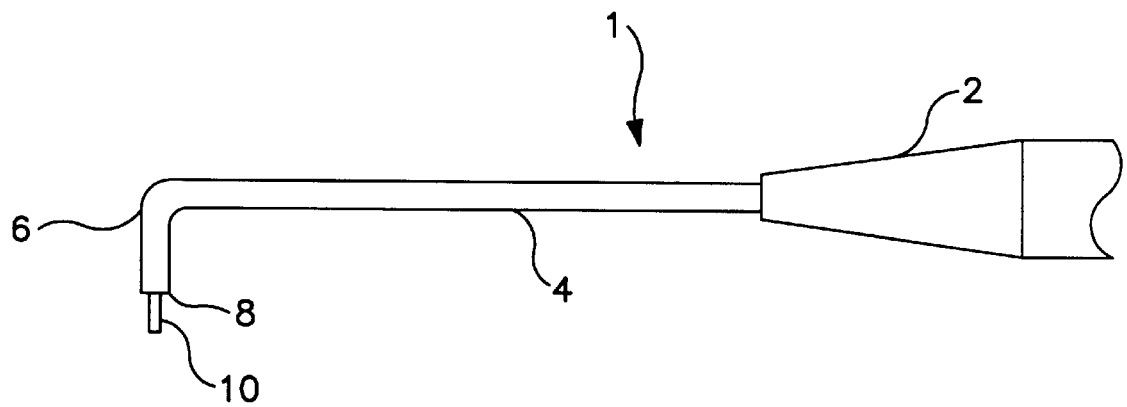
FIG. 1 illustrates a parallel dual prong bipolar electrode.

The methods and apparatus of the present invention relate to bipolar electrocoagulation to preserve and restore the health of the dental pulp. While procedures for preserving the health of the dental pulp are currently available, the present invention expands this capability to teeth with larger pulp exposures which were heretofore not amenable to pulp therapy. Despite the teaching in the prior art, the methods of the present invention are not limited by the size of the pulp exposure.

The mildest form of pulpal involvement are those teeth with pulps which are exposed and which do not include any significant pre-treatment pulpal pathology. The pulps of these teeth are typically exposed (1) inadvertently while restoring the tooth for objectives unrelated to the pulp; (2) intentionally exposed to allow alignment of the tooth with other teeth during crown and fixed bridge procedures; and (3) intentionally exposed when the teeth are trimmed to the level of the gum and used for support of an overdenture. Teeth which have been inadvertently exposed have been treated frequently and successfully using calcium hydroxide and more recently resin 'capping materials' when the pulp exposure was small. With moderate or large exposures, pulp capping was not applied routinely or effectively.

Pulps exposed during tooth reduction for crowns (caps) or fixed bridges were pulp capped less frequently and were usually directed to endodontic procedures. This was because pulp capping has not been considered a predictably successful procedure even with asymptomatic pulps and small exposures. In contrast, endodontic therapy is viewed as a predictable mode of treatment (90+ percent success). Rather than risk having to perforate the permanent crown for access in accomplishing endodontic therapy after the crown has been cemented, teeth were often referred for endodontic therapy upon exposure of the pulp and prior to fabricating the permanent crown. Another disadvantage with crown procedures, is that tooth reduction at the pulp exposure site did not provide space for capping materials and such materials often dislodged. The present invention overcomes this problem by specifically designing the exposure site for the pulp barrier material, i.e., the pulpal wall is prepared with retention form, resistance form, and space for the resinous barrier material in the actual restoration of the wall.

The present invention also provides for teeth (intentionally) exposed for use under overdentures. Teeth are trimmed to the level of the gum typically exposing the pulp. Such teeth have routinely been treated with endodontic therapy. No successful efforts at maintaining the integrity of the pulpal tissue in the root portion can be found in the literature. The present invention preserves the integrity of the remaining pulp tissue by a specific preparation of the exposure site and restoration of the opening with a resinous barrier. The present invention accordingly allows teeth to be saved and improves the stability and function of traditional complete dentures.

Teeth exhibiting pulpal inflammation (pulpitis) and without accompanying periapi cal lesions are considered to include greater pathology than the intentional or mechanically exposed pulps since these pulps have been exposed to bacteria contained in the carious lesion or directly to the oral cavity. These teeth are routinely diagnosed as "irreversible pulpitis" and relegated to endodontic therapy or extraction. When acute pain is associated with other clinical tests, the decision to treat endodontically is more universal by current criteria. The present invention treats the dental pulp as opposed to removing the pulp or tooth in all degrees of pulpitis. These diseased teeth may range from nuisance level of discomfort to the acutely painful tooth typically referred to as a toothache or abscessed tooth.

Teeth exhibiting a periapical lesion (apical periodontitis) are considered the most severe form of pulpal inflammation just short of necrosis. (A periapical lesion is inflammation extending beyond the pulp to the tissue and bone around the apex of the root, hence the term "periapical". Such lesions are characterized by a breakdown of the bone resulting in a radiolucency on x-rays.) Many dentists assume that the pulp is necrotic when such a lesion is seen on a dental radiograph. The presence of a periapical lesion is almost universally accepted as an irreversible pulpitis or necrosis of the pulp. Indeed, while terms such as "degenerating" or "degenerated" periapical lesion delineating the various states of pulpal pathology are described in dental texts, no comparable terms such as "regenerating" periapical lesions are included in the classification systems. This clearly signifies that the potential for pulpal healing or treatment is not currently acknowledged by the dental profession.

While a necrotic pulp may be irreversible, pulpal and periapical inflammation may be successfully treated using the apparatus and methods of the present invention. In particular, the methods and apparatus of the present invention facilitate reversal of periapical lesions.

B. Hemostasis

Before describing specific features and applications of bipolar electrocoagulation in pulp therapy and restorative dentistry, the importance of the present invention to hemostasis should be understood.

Hemostasis is described in the medical literature to occur in one of ways: (1) Coaptive—whereby the vessel is grasped and clipped, ligated, coagulated (electrosurgically welded), or otherwise closed by bringing the walls of the vessels together. This form is typically used with larger vessels and may also involve coagulation of the vessel contents and shrinkage of the vessel walls; (2) Obliterative—whereby the vessels and contents are chemically treated or coagulated (by electrosurery or laser) so that the resulting shrinkage of the vessel walls and blockage of the vessel lumen by the coagulated vessel contents enables control of bleeding. This form is typically used with small blood vessels where grasping of the vessel would be difficult or impossible. Only the obliterative form of hemostasis is applicable to pulp therapy. Vessels are typically very small and access to vessels is impossible as they are encased in a small chamber with hard tissue walls (dentin).

While lasers can create precise coagulation of the surface tissue, precision is essentially compromised by the presence of blood on the surface of the pulp or other tissue. With a laser, and previous monopolar or bipolar electrocoagulation methods, blood is coagulated as well as the tissue. The impact of the electrical current or laser beam is affected by the coagulating blood thus compromising the precision of coagulation even though some coagulation will occur. The present invention supersedes laser applications in pulp therapy. For example, a coaxial electrode can be positioned in direct contact with the exposed pulp tissue despite a pool of blood and the surface of the tissue can be precisely coagulated.

The precise coagulation of the present invention allows the creation of a layer of desiccation. The term "desiccation" refers to a specific level of coagulation between white coagulation, which is coagulation at a lower temperature and black coagulation, which is coagulation at a higher temperature often resulting in charring of the tissue. Desiccation has been described in the medical literature as the optimum level of coagulation for hemostasis.

C. Bipolar Electrocoagulation

There are two types of electrosurgery, monopolar and bipolar electrosurgery. Electrosurgery has been in use in medicine and dentistry for almost a century. In dentistry, it has been limited exclusively to the monopolar variety except for limited use of bipolar electrosurgery by oral surgeons. Both monopolar and bipolar modes use an alternating electric current with a sinusoidal waveform in the frequency range 500 KHZ to 4.0 MHZ. The monopolar mode was the first to be developed (over a century ago) while the bipolar mode was introduced by a neurosurgeon in the 1940's (Greenwood, J., Arch. Phys. Ther., 23:552–554 (1942)). Both modes can generate coagulation of tissue while the monopolar mode is superior in cutting capability. The high frequency current possesses both traditional electric current properties and radiating properties. The significant difference between the two modes is the path of the dissipating current.

In the bipolar mode, the dissipating current flows directly to the dispersive electrode which is typically the same size and very close to the active electrode (Greenwood, supra refers to it as "two point coagulation"). The only tissue involved in the dissipating current is the tissue between the two electrodes. Thus bipolar electrosurgery provides substantially greater safety by avoiding involvement of major vessels, nerves, or other critical tissues or organs. The bipolar mode requires approximately 20% of the current to create the same degree of coagulation—an additional safety feature by reducing the potential for capacitive coupling.

The present invention applies a combination of either a dual-prong or a coaxial electrode with a bipolar microsurgical unit to generate precise coagulation on the dental pulp without deep injury to the pulp. The present invention represents the first application of bipolar electrosurgery of any form for hemostasis in pulp therapy. The combination of bipolar electrodes, bipolar microsurgical unit, and electronic timer generates an even higher level of precision and safety when coagulating the surface of the dental pulp.

D. Electrodes

Bipolar electrodes can be categorized in one of three groups: (1) Bipolar forceps with each forceps tip individually wired are used to grasp tissue or vessels for coagulation; (2) Two-prong electrodes with a fixed distance between the electrodes which allows coagulafion of the tissue between the two points. Two point electrodes have been adapted in the present invention to enable coagulation of pulpal and gingival tissue; and (3) Coaxial electrodes utilized in ophthalmic surgery which consist of an outer tube and an inner insulated wire. Coagulation occurs in a circular 'footprint' approximately the size of the end of the electrode. The present invention has adapted and refined the use of the coaxial electrode for use in pulp therapy.

For purposes of bipolar coagulation, blood is a conductive tissue and substantially influences the degree of coagulation, zone of coagulation, optimal power output, and the path of the current. Indeed, blood behaves much like tissue and in some aspects is more susceptible to coagulation. For example, relatively dry tissue is less susceptible to coagulation than moist tissue. This is probably due to the conductivity at the interface of electrode and tissue. Blood enhances the conductivity at the interface. Unfortunately, it also allows dissipation of the electrosurgical current creating a wider and unpredictable zone of coagullation. These variations apply to monopolar electrosurgery and to most forms of bipolar electrosurgery. An important exception is the bipolar coaxial electrode. Blood in the field influences the behavior of the coaxial electrode minimally provided the electrode is placed in contact with the surface of the tissue and not just in contact with blood. Typical bipolar electrodes, on the other hand, will coagulate both the blood and tissue affecting the power delivered to the tissue. The exposed prongs of the other electrodes allow dissipation of current around the electrode creating a more diffuse coagulation. The highly desirable precision in coagulation is lost.

The selection of a coaxial bipolar electrode [as opposed to a parallel fixed-position dual-prong electrode (FPDP) or a variable-position dual-prong electrode (VPDP, forceps-type)] is a crucial factor in establishing a high level of consistency in treatment of dental pulps. In pulp therapy, a very shallow zone of coagulation is critical to the success of pulp therapy. The coaxial electrode is self-limiting in area and depth of coagulation and the area of coagulation is more consistent (a circular zone of coagulation determined by the 'footprint' of the electrode) than other types of electrodes. Furthermore, the total zone of coagulation is much more consistent than with other types of electrodes. The current at the active electrode (inner insulated wire) is limited in flow to the encircling outer dispersive electrode confining the coagulation to the diameter of the outer tube (dispersive electrode). As the current coagulates the tissue as it emerges from the inner active electrode, the resulting increased resistance (impedance) of the tissue prevents further or deeper coagulation.

Coagulation in the bipolar mode always requires contact of the electrode with the tissue. However, with the FPDP and VPDP electrodes if the electrode penetrates the tissue surface, additional coagulation will occur throughout the length of the immersed segments of the electrode. Indeed, the depth of penetration will proportionately determine the depth of coagulation. This is undesirable in pulp therapy. The coaxial electrode behaves differently. Since the active electrode is encased within the dispersive electrode and since there is no tissue between the active and dispersive electrode except where the active electrode exits the dispersive electrode, coagulation is limited to the end-surface of the electrode. Furthermore, as soon as the tissue at the tip of the electrode becomes coagulated, the impedance increases preventing further flow of current (within reasonable power levels). Therefore, the zone of coagulation varies little whether the coaxial electrode touches only the surface or penetrates the surface. Under both conditions, the resulting coagulation takes the form of a thin disc with the diameter of the electrode. Coagulation along the shaft of the coaxial electrode does not occur.

Figure 2:
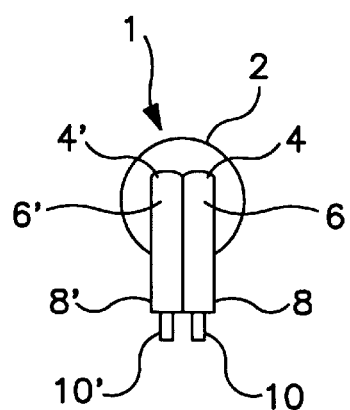
FIG. 2 illustrates a front view of the dual prong bipolar electrode of FIG. 1.

Referring now to FIG. 1 which illustrates a side view of a dual prong parallel bipolar electrode 1, and FIG. 2 which is a front view of the dual prong parallel electrode of FIG. 1, the electrode has a handle 2, with insulated shafts 4, 4' which project from the handle 2. At the distal end of the shafts 4, 4' there are angular bends 6, 6' where the insulation 8, 8' ends, exposing the two electrode prongs 10, 10'.

FIG. 2 illustrates the substantially parallel relationship between the two lectrode probes 10, 10'.

In embodiments utilizing a dual-prong parallel electrode, the electrode preferably comprises about 22 gauge prongs with about a 1.0 mm interprong distance, or about 25 gauge prongs with about a 0.5 mm interprong distance. The general dimensions of the handle, shaft, angular bend, and electrodes may be any size suitable for use in a patient's mouth. Preferably, the electrode prongs 10, 10' are substantially parallel beyond the angular bend 6, 6' aiid are insulated to about halfway from the tip of electrode to the angular bend on both prongs. The angle at the angular bend may be any suitable angle for facilitating use in a patient's mouth, preferably about 60° to about 135°, most preferably about 90°. The insulation on the electrodes is preferably a thin layer. In preferred embodiments, the shafts 4, 4' should be rigid. The shaft insulation should supplement the shaft's rigidity and this rigidity should extend slightly beyond the angular bend to ensure that the extended electrode prongs maintain parallelism and the correct inter-probe distance. The electrode includes means for connection to a power source.

A coaxial electrode useful for pulp therapy will preferably include the following: a handle with a front end, a middle region which consists of a pencil-like grip, and a rear portion having a two-prong male connector. This two-prong connector attaches to a twin wire cord leading to an electrosurgical power supply: A coaxial electrode is attached to the front end of the handle. The coaxial electrode consists of a hollow tube of stainless steel, titanium, nickel or other suitable alloy traditionally used in electrosurgery. The hollow tube contains a thin wire of similar alloy with an intervening layer of insulation between the wire and the tube. The hollow tube is wired to one of the rear prongs while the inner wire is connected to the other rear prong. This front-end assembly comprises the coaxial portion of the electrode. The coaxial segment may be permanently attached to the handle segment or an alternative approach is to provide a reusable handle with a removable or interchangeable coaxial component that interconnects with a two-contact receptacle front-end.

Assuming the operator's fingers would grasp the handle at the most forward position, the coaxial segment is preferably long enough to reach the most posterior tooth in the mouth (third molar) without necessitating the insertion of the operator's fingers far into the patient's mouth.

The coaxial component may be provided in various diameters (about 18 gauge to about 25 gauge) with the most distal segment sharply curved at various angles. The electrodes would preferably have the internal angle of the distal segment (relative to the long axis) ranging from about 60 to about 135 degrees and preferably the distal segment would extend about 5 to about 20 mm beyond the angled region to enable access to exposures in all areas of the teeth.

Figure 3:
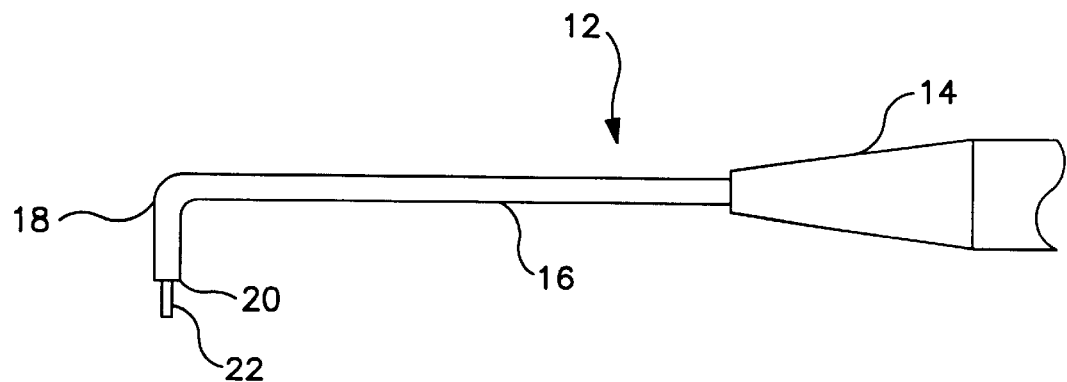
FIG. 3 illustrates a coaxial bipolar electrode.

An example of a coaxial bipolar electrode useful in the practice of the present invention is illustrated in FIG. 3 which illustrates a side view of a coaxial bipolar electrode 12, the electrode has a handle 14 with an insulated shaft 16 which projects from the handle 14. At the distal end of the shaft 16 there is an angular bend 18 where the insulation 20 ends, exposing the coaxial electrode probe 22.

Figure 4:
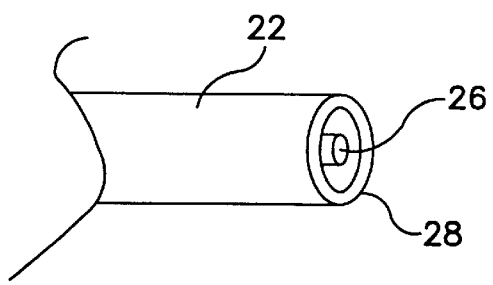
FIG. 4 illustrates a partial perspective view of the coaxial bipolar electrode of FIG. 3.

FIG. 4 is a partial perspective view in an enlarged scale of the coaxial bipolar electrode 22 of FIG. 3 in which the coaxial relationship between the active 26 and dispersive 28 electrodes is illustrated.

A variety of coaxial electrodes may be utilized in the present invention. Three gauges, 18 g, 20 g, 23 g are preferred in the practice of the invention. A standard handle is available from Kirwan Ophthalmic Bipolar Penils, Catalog Nos. (14-5002/14-7002). In preferred embodiments, the electrodes have a dome tip. The shaft 16 is preferably insulated from the handle to the angular bend 18. The angle at the angular bend may be any suitable angle for facilitating use in a patient's mouth, preferably about 60° to about 135°, most preferably about 90° with little or no compression of the coaxial frame.

The electrodes include means for connection to a power source, such as an Elmed Microsurgery Unit (Elmed, Inc., 60 West Fay Street, Addison, Ill. 60101). The handles and insulating materials may be made from conventional materials known in the art, such as plastics, including teflon. The electrode probe section is preferably long enough to facilitate use in a patient's mouth with relatively easy access to teeth in need of treatment.

When coagulation occurs, the coagulated tissue has a tendency to stick to the electrode tip. If not removed, the coagulant layer reduces the effectiveness of the electrode. The choice of alloy and polishing procedures used on the electrode tip can influence the degree of "sticking" of the coagulated tissue. The optimal alloy used in the electrode would be determined based primarily on a determination of which alloy provided the greatest conductivity while resulting in minimal sticking of coagulated tissue. Accordingly, the electrodes used in the present invention are made of any suitable conducting material, preferably from a non-sticking nickel and/or stainless steel alloy. The tips of the electrodes preferably have a dome-like shape.

E. Electrosurgical Unit

The electrodes are preferably used with a bipolar electrosurgical unit (ESU), which includes a timer to control the impulses in fractions of a second. The timer can be regulated by the operator and is pre-set for the specific electrode, ESU and power level to be used Some units include timers for specific therapeutic objectives (e.g. coagulation for reduction of the size of the uvula (8 sec range)).

Many bipolar electrosurgical units are available with a variety of current frequencies and current types (e.g various waveform types, damping, work cycle).

The general requirements for a bipolar ESU are as follows:

Power Output: 0–20 watts as measured against 100 Ohm resistance
Power Supply: 115 V, 60 Hz (optional 220 V, 50 Hz)
Frequency: Optimum 500 KHZ (other frequencies will also work)
Current: Optimum—smooth, non-modulated, continuous RF-current (other currents will also work with appropriate calibration with electrodes.)
Cable: Teflon coated twin-wire 6–10 foot cable The ESU preferably has power output in the range of about 0.0 to about 20.0 watts. A number of criteria define what frequencies should be used with the unit. Firstly, a frequency must be sufficiently high to prevent stimulation of muscles and nerves. Available electrosurgical frequencies are well above these levels. Secondly, heat is generated by the rapid oscillation of charged molecules caused by the alternating polarity of the alternating electrosurgical current. This is referred to as the dielectric effect and increases with an increase in the frequency of the alternative current. What portion of the heat generated is due to the dielectric effect and what portion is due to resistance (impedance) of the tissue is unclear. Frequencies in the range of 0.5 to 4.0 MHZ are typically used in electrosurgery with the most often used frequencies occurring in the 0.5 to 2.0 MHZ. Thirdly, the higher frequencies (3.0 to 4.0 MHZ) result in more current loss due to the radiating properties of electrosurgical currents. This factor encourages the use of lower frequencies.

Low power microsurgical units range from 0–15 watts, while high power units used for prostate resection can provide 300 or more watts. Based on the type of tissue, the volume of tissue, and the precise nature of coagulation desired in pulpal hemostasis, an electrosurgical unit providing power output in the range of 0–20 watts (measured against 100 Ohm resistance) is preferred.

The ESU of the present invention preferably includes an electronic timer which can be set for the appropriate time intervals for each electrode (0.05 to 0.5 sec) to create the optimal level of coagulation. The optimal level of coagulation is determined by establishing durable hemostasis with minimal surgical wound. Durable hemostasis can be ascertained clinically using (1) vital pulps, (2) an intact circulation, (3) actual pulp tissue, and (4) conditions and circumstances that will be confronted in actual pulp therapy. Minimal surgical wound can be observed and established with each electrode design by utilizing the electrode on tissue specimens such as beef steak, beef liver, animal intestinal walls, or animal blood vessels. An example of how to determine the optimal level of coagulation is presented in Example 2 hereinbelow.

The implementation of the timer enables another level of safety and precision when attempting to coagulate extremely small areas and for extremely shallow depths. The combination of a ESU, a coaxial electrode, and a timer allowing intervals in fractions of a second enables the ultimate precision in coagulation. Once the tissue at the end of the electrode coagulates, the increased resistance (impedance) of the tissue prevents flow of current. This self-limiting capability of the coaxial electrode replaces more complex systems, e.g. impedance monitoring of the active electrode or temperature monitoring of the tissue at the active electrode.

The methods of the present invention establish an electrosurgical application with unprecedented precision. The methods of the present invention have as their goal a specific therapeutic objective: to create the desiccated form of coagulation on a small area of one type of tissue (dental pulp). This is possible in part because the tissue to be coagulated is fairly uniform in composition compared to the tissue encountered in most other surgical procedures.

In order to establish the optimum power/time settings ("hemostatic combination"), the type of electrode, the size of each pole of the electrode, the type of metal composing the electrode and numerous other aspects must be considered to optimize treatment.

The optimal configuration for the electrode is established by the location and size of the most typical exposures expected to be confronted. Since most exposures occur because of decay on the mesial and distal sides of teeth (between teeth), the typical electrode would have a right-angle bend with a 10 mm extension beyond the bend. Preferably an about 18 gauge electrode is used to treat lesions due to decay while an about 23 gauge electrode is preferably used for coagulation within the root portions in overdenture applications.

The optimal power/time combination will provide uniform cogaulation throughout the footprint of the electrode. An example of how to determine the optimal power/time combination is presented in Example 3.

The coaxial design provides the most consistent, shallow, and optimal form of coagulation with the greatest safety and minimal surgical wound. By relying on bipolar coagulation and a specific coaxial electrode, the volume of tissue to be coagulated is consistent, and by relying on the bipolar mode and using a coaxial electrode configuration, the path of the current is consistent. The frequency and current type of the ESU is established by the manufacturer which are initially factored in the calibration of the 'hemostatic combination' and therefore consistent. The use of a pre-determined optimal time which has been found to be in fractions of a second (e.g. 0.5 sec impulse) provides another level of consistency. Given the difficulty in manually controlling the output of the ESU in fractions of a second, the timer is an important component in providing consistency and a greater level of safety to the pulp.

F. Pulp Barrier

The present invention includes use of components for replacing the lost pulpal wall. These components are included to provide retention for the pulp barrier independent of the external restoration. The long term integrity of the pulp barrier: (1) should not be linked to the stresses applied to the external restoration; (2) should not be determined by the success/failure of the external restoration; and (3) the pulp barrier should not provide the principal support or retention for the external restoration. The external restoration should rely on traditional cavity preparation components for retention and resistance to prevent displacement outward. This protocol, however, emphasizes the incorporation of retentive components to also prevent inward displacement of the external restoration. Contrary to recommendations by many lecturers and manufacturers of adhesive restorative materials, the adhesion that occurs between a resinous pulp barrier and an adhering external restoration should be directed to preventing microleakage and not relied upon for the basic retention of the restoration. If and when an external restoration fails or needs replacement, ideally the pulp barrier should remain intact. Traditional cavity preparation components for retention include undercuts, grooves, or threaded pins.

The material used for replacing the lost portion of the pulpal wall preferably comprises an adhesive resin barrier material which creates an effective hybrid layer and is biocompatible with the pulp. A variety of resinous materials may also prove useful as a long-term pulp barrier.

A wide range of resins have been introduced in dentistry to achieve adhesion between the dentin and the external restoration with the objective of reducing microleakage and the ingress of bacteria from the oral cavity to the internal walls of the cavity preparation. With a substantial dentinal wall remaining over the pulp, the biocompatibility of the resins with the pulp is not an important concern. However, when such resins are applied in direct contact with pulpal tissue, the biocompatibility issue is crucial.

The present invention goes beyond current procedures to utilize resins as the restorative material to reconstruct the missing pulpal wall. Hence, the resin is referred to as a "pulp barrier" rather than a "pulp capping" material. Traditional pulp capping materials served to provide medicaments to the pulp, to provide thermal protection (insulation), and to stimulate reparative dentin via a mild irritating effect on the pulp.

A preferred resin material is a 4-META adhesive resin system (Metabond C&B; Parkell Dental Products, Farmingdale, N.Y.) which can be used to replace the missing segment of the pulpal wall and which has demonstrated the ability to create an effective seal (hybrid layer). The 4-META resin may be applied according to the instructions of the manufacturer. Studies support a degree of biocompatibility with pulpal tissue.

Preferably the resin used to restore the pulpal wall includes a visible dye such that the resin is color coded, serving to warn dentists performing subsequent procedures not to violate the pulpal wall barrier. A variety of dyes are known in the dental arts, and any dye that is non-toxic and which retains its color are preferably used in the practice of the invention.

EXAMPLES

Example 1

Pulp Hemostasis Method

The following example describes the use of the methods and apparatus of the present invention for pulp hemostasis.

The tooth is examined clinically and radiographically. Clinical symptoms are recorded for comparison with subsequent evaluations. Evidence of periapical inflammation is also noted (tenderness to percussion of the tooth and apical radiolucency). Vitality of the tooth is determined by sensitivity to ice, electric pulp testing, or sensitivity to instrumentation such as cavity preparation prior to local anesthetic. If the pulp is diagnosed as necrotic, the tooth is planned for extraction or endodontic therapy since pulp therapy is not possible.

Once vitality is established the tooth is anesthetized with local anesthetic. If the carious lesion does not extend subgingivally, a rubber dam may be placed for improved isolation.

The outline form for the planned cavity preparation is completed according to traditional guidelines avoiding temporarily the removal of deep caries. Deep caries excavation with the probable exposure of the pulp is postponed until the majority of the cavity preparation is completed to minimize debris from entering the pulpal space.

Once the cavity preparation is completed, deep caries is removed with a large sharp spoon excavator or a round bur on a low speed handpiece.

Caries excavation is completed despite initial exposure of the pulp. Thorough excavation of caries should be accomplished. Unlike past 'pulp capping' procedures in which the prognosis was considered better if the exposure was kept small, in vital pulp therapy described in this protocol the prognosis is improved by removal of all affected and compromised dentin. [Affected and compromised refers to the (1) decalcification of the remaining dentin, (2) inclusion of bacteria or bacterial by-products, and (3) potential collapse of thin areas of dentin.] Vital pulp therapy encourages more thorough removal of caries and affected dentin.

Bleeding of the pulp during caries excavation and cavity preparation should be encouraged since the flushing action of the bleeding will reduce the debris that may become incorporated in the pulp.

Once the cavity preparation is completed, vitality of the pulp is confirmed by the presence of both blood (intact circulation) and pulp tissue. Blood alone can sometimes occur from the apical region or from another canal despite a necrotic pulp in one or more canals. Instrumentation and materials are then prepared for hemostasis and formation of the pulp barrier (restoration of the pulpal wall).

A Storz 18 g coaxial bipolar electrode used in ophthalmology is used to provide hemostasis in pulp therapy utilizing an Elmed Micro Electrosurgery Unit with power output (against 100 Ohm resistance) of about 0 to about 20 watts and a frequency of 500 MHZ. the unit is combined with an electronic timer providing 0.5 sec interval of power with each press of the foot switch. The power setting of the unit is set to #6 providing 5 watts of power at the unit (determining the actual power at the tissue surface is difficult and may vary for many reasons; e.g. length of cable, deterioration of cable, radiating potential of high frequency causing current loss, etc). The electrode is attached to the unit via a 6 foot teflon covered cable.

The coaxial electrode is placed in contact with the pulp tissue and the foot control is engaged to provide one impulse of 0.5 sec duration. If the exposure is larger than the end of the electrode and bleeding is occurring from other points, the electrode is moved and another 0.5 sec impulse is applied. This sequence is continued until the entire surface of the pulp is coagulated. The size of the exposure is inconsequential. If one of the impulses did not achieve hemostasis, another impulse can be applied over the same area. By using the coaxial electrode, the depth of coagulation is not cumulative but more 'compensatory,' i.e. tissue already coagulated develops a higher resistance (impedance) and inhibits further coagulation while adjacent unaffected tissue will be susceptible to coagulation. The coaxial electrode has the capability to control the flow of current to the area immediately under the electrode tip. Indeed the same area can receive numerous coaxial impulses with virtually no increase in depth of coagulation. Rarely will it be necessary to increase the power, and when that option is selected it is increased only one setting (approx. 1–2 watts).

Once hemostasis is achieved, it is checked for durability by swabbing the pulpal surface with a cotton pellet moistened with water or saline. If bleeding recurs, coagulation is repeated. Specific bleeding points will be more visible and readily coagulated since most vessels have been sealed previously. The durability check is important since it is crucial that bleeding does not recur while the barrier is being formed.

Once durable hemostasis is accomplished, an adhesive resin barrier material which creates an effective hybrid layer and is biocompatible with the pulp is applied according to the instructions of the manufacturer. (4-META adhesive resin system (Metabond C&B; Parkell Dental Products, Farmingdale, N.Y.).) The material is applied in increments with a brush tip to minimize the polymerization shrinkage. Additional retentive components may be incorporated after complete setting of the barrier material. The remaining dentin and enamel are prepared for a sealed external restoration.

The external restoration is then placed according to traditional procedures.

The patient is recalled 3, 6, and 12 months for recall evaluation using the same criteria as the pre-treatment examination.

Example 2

Determination of Optimal Coagulation

A new coaxial electrode with a given outer diameter will be coupled with a Elmed Microsurgical Unit and a six-foot cable. The optimal and consistent coagulation ("hemostatic combination") for that electrode will be defined by (1) uniform coagulation throughout the electrode "footprint" (surface area of the end of the electrode tip), and (2) minimal depth of coagulation (0.25 to 0.5 mm depth). By varying the power output to the electrode one will observe, with insufficient current, that a "donut" configuration of coagulation occurs with an inner zone of uncoagulated tissue and an outer rim of coagulation following the outline of the outer tube of the electrode. As the power output is increased, the zone of coagulation becomes uniform throughout the entire surface (footprint) of the electrode tip. Further increasing the power output is redundant with the coaxial electrode. The coaxial electrode is self-limiting in coagulation which is one of the highly-valued properties and safety features for applications in pulp therapy. Increasing the power output with other types of electrodes increases the "area" of coagulation, the "depth" of coagulation and the "degree" of coagulation proceeding from the lower acceptable levels of white coagulation, through the optimal level of desiccation, to the higher unacceptable levels of black coagulation (charring).

Thus by varying the power levels and impulse time intervals, an optimal "combination" can be established for each electrode design and size.

Example 3

Determination of Optimal Power and Time Settings for ESU

To establish the optimal power/time combination, the electrode would be used on liver tissue beginning with a fixed time interval selected within a reasonable range of 0.01 to 1.0 seconds. While intervals in the range of several seconds at very low power would also create coagulation, substantial lateral heat and a broader area of coagulation would occur which is not desirable. Beginning with the lowest power setting on the electrosurgical unit, areas would be coagulated on the liver until the optimal coagulation zone is achieved (uniform coagulation throughout the "footprint" of the electrode). The power would be increased further to ascertain that the lower power levels provided the optimal coagulation.

Figure 5:
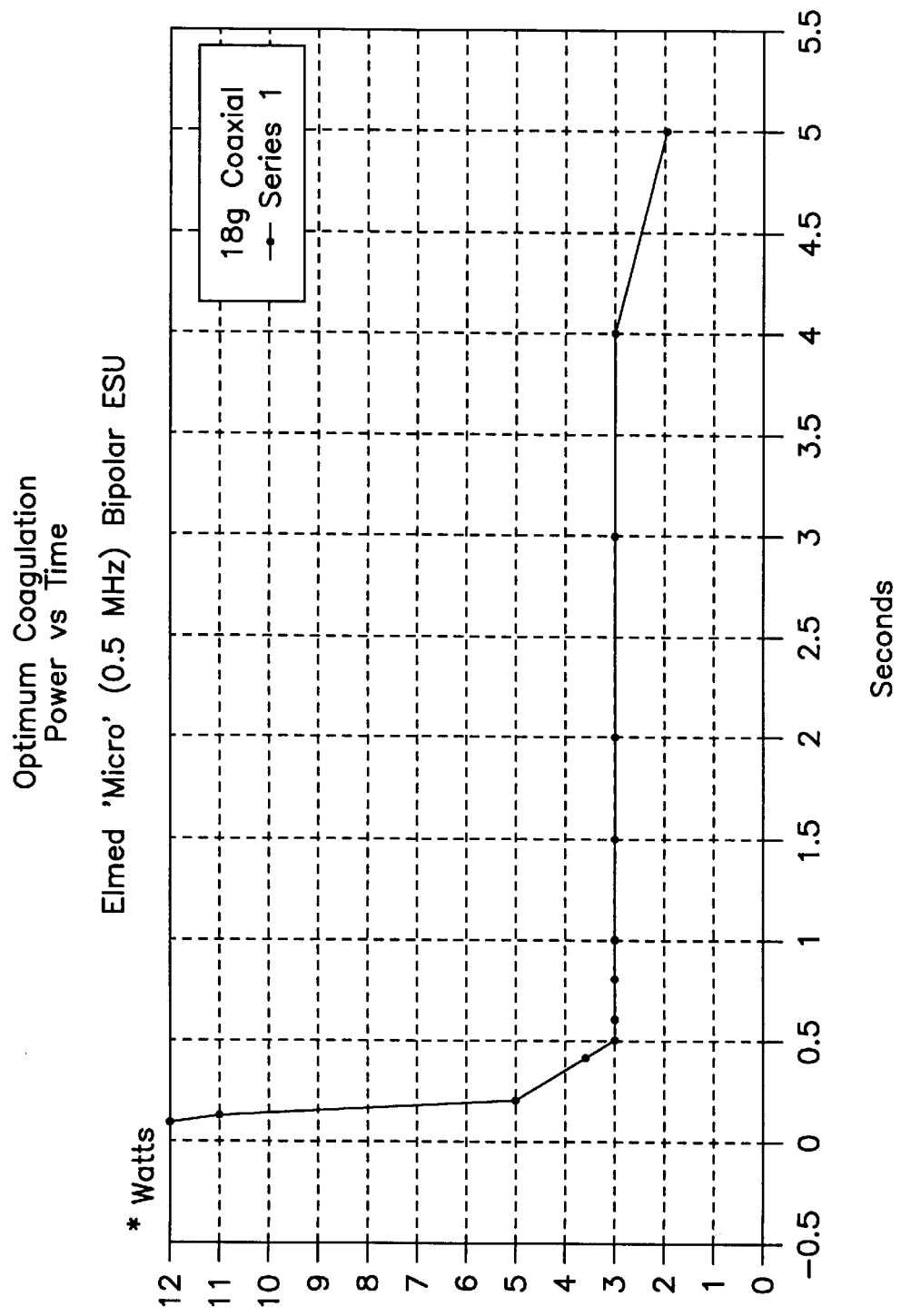
FIG. 5 is a graph used to determine the optimal time and power settings for coagulation.

One of the lowest power output levels that achieved optimal coagulation would then be selected (several levels may be available) as the fixed power output level. The same process would be repeated by varying the time interval to establish the minimum time intervals that provide the optimal zone of coagulation. Once both series are plotted, the minimal time is coupled with the minimal power to establish the optimal combination for that electrode design. Although several combinations may be found suitable, they will all fall within a narrow range. An optimal time/power "hemostatic combination" can readily be established in the mid-range providing some latitude for the operator. Such a graph is provided in FIG. 5 to illustrate how definitively the optimum combination can be established.

What is claimed is:

1. A method for controlling the bleeding in an exposed dental pulp in a patient performing bipolar electrocoagulation of said pulp.

2. The method of claim 1 in which said electrocoagulation is performed with a two-point bipolar electrode.

3. The method of claim 1 in which said bipolar electrode is a fixed parallel dual-prong (FPDP) electrode.

4. The method of claim 1 in which said electrocoagulation is performed with a coaxial bipolar electrode.

5. The method of claim 1 wherein said electrocoagulation is performed using an apparatus for bipolar electrocoagulation of dental pulp comprising a bipolar electrode connected to a low power electrosurgical unit.

6. The method of claim 5 further comprising an electronic timer attached to said electrosurgical unit which regulates the duration of the power supplied to said electrode.

7. The method of claim 6 wherein said bipolar electrode is a coaxial electrode which limits coagulation to the surface area of the tip of said electrode.

8. The method of claim 6 wherein said timer enables minimal and prescribed coagulation of pulp by the application of microsecond impulses of power to said pulp.

9. A method for creating a coagulated tissue layer on the surface of an exposed dental pulp in order to reconstruct the pulpal wall comprising exposing said pulp to bipolar electrocoagulation.

10. The method of claim 9 in which said electrocoagulation is performed with a two-point bipolar electrode.

11. The method of claim 9 in which said bipolar electrode is a fixed parallel dual-prong (FPDP) electrode.

12. The method of claim 9 in which said electrocoagulation is performed with a coaxial bipolar electrode.

13. The method of claim 1 further comprising application of resin to said pulp.

14. The method of claim 13 wherein said resin is color-coded.

* * * * *

UNITED STATES PATENT AND TRADEMARK OFFICE
CERTIFICATE OF CORRECTION

PATENT NO. : 6,319,007 B1
DATED : November 20, 2001
INVENTOR(S) : Livaditis

It is certified that error appears in the above-identified patent and that said Letters Patent is hereby corrected as shown below:

Column 14,
Line 64, after "patient" insert -- comprising --.

Column 15,
Line 1, change "claim 1" to -- claim 2 --.

Column 16,
Line 7, change "claim 9" to -- claim 10 --.

Signed and Sealed this

Twentieth Day of August, 2002

Attest:

JAMES E. ROGAN
Attesting Officer  Director of the United States Patent and Trademark Office